(12) United States Patent
Landes et al.

(10) Patent No.: US 6,362,133 B1
(45) Date of Patent: Mar. 26, 2002

(54) SYNERGISTICALLY ACTIVE HERBICIDAL MIXTURES

(75) Inventors: Max Landes, Gönnheim; Bernd Sievernich, Böhl-Iggelheim; Elmar Kibler, Hassloch; Wessel Nuyken, Otterstadt; Helmut Walter, Obrigheim; Karl-Otto Westphalen, Speyer; Horst Mayer, Ludwigshafen; Egon Haden, Harthausen; Christiaan Mulder, Nelspruit; Alfons Schönhammer, Mertesheim; Gerhard Hamprecht, Weinheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/520,224

(22) Filed: Mar. 7, 2000

Related U.S. Application Data

(62) Division of application No. 09/043,314, filed as application No. PCT/EP96/03996 on Sep. 12, 1996, now Pat. No. 6,054,410.

(30) Foreign Application Priority Data

Sep. 20, 1995 (DE) .......................................... 195 34 910

(51) Int. Cl.[7] .......................... A01N 43/54; A01N 43/66
(52) U.S. Cl. ...................... 504/128; 504/132; 504/133; 504/134; 504/136
(58) Field of Search ................................. 504/128, 132, 504/133, 134, 136

(56) References Cited

U.S. PATENT DOCUMENTS 5,071,470 A * 12/1991 Mayer et al. ................... 71/93
5,478,798 A * 12/1995 Mayer et al. ................ 504/212

* cited by examiner

Primary Examiner—S. Mark Clardy
(74) Attorney, Agent, or Firm—Keil & Weinkauf

(57) ABSTRACT

A composition which comprises
a) at least one sulfonylurea of the formula I:

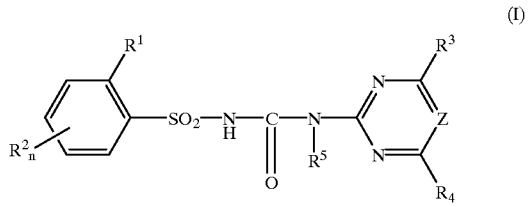

wherein the radicals $R^1$ to $R^5$ and the index n are as defined in the specification, or an enviromentally compatible salt of the sulfonylurea, and
b) at least one herbicidal compound selected from groups $b_1$ to $b_{41}$ as defined in the specification, or an environmentally compatible salt of the herbicidal compound, and which exhibits a synergistic herbicidal effect.

20 Claims, No Drawings

SYNERGISTICALLY ACTIVE HERBICIDAL MIXTURES

This is a Divisional Application of application Ser. No. 09/043,314, filed on Feb. 17, 1998, under 35 U.S.C. §371 now U.S. Pat. No. 6,054,410, which is a 371 of PCT/EP96/03996 filed Sep. 12, 1996.

The present invention relates to a synergistically active herbicidal mixture composed of a sulfonylurea derivative (a) of the formula I and one or more herbicidal compounds b1 to 41.

Herbicidally active sulfonylureas of the formula I have been disclosed in the prior art, for example in EP-388 873, EP-559 814, EP-291 851 and DE-40 07 683 and the Conference Proceedings "Fluorine in Agriculture", Jan. 9–11 1995, Manchester, chapter "New Fluoro Intermediates for Herbicidal Sulfonylureas".

Herbicidal compounds b1 to b41 are described, for example, in "Herbizide", Hock, Fedtke, Schmidt, 1st Edition, Thieme 1995 (see "quinclorac" p. 238, "molinate" p. 32, "butachlor" p. 32, "pretilachlor" p. 32, "dithiopyr" p. 32, "mefenacet" p. 32, "fenoxapropethyl" p. 216, "dimepiperate" p. 32, "pyrazolate" p. 146, "pyrazoxyfen" p. 146, "bensulfuron-methyl" p. 31, "pyrazosulfuron-ethyl" p. 31, "cinosulfuron" p. 31, "benfuresate" p. 233, "bromobutide" p. 243, "dymrone" p. 243, "dimethyametryn " p. 118, "esprocarb" p. 229, "pyributicarb" p. 32, "cinemthylin" p. 32, "propanil" p. 32, "2,4-D" p. 30, "bentazone" p. 30, "DPX-A-8947" p. 175, "mecoprop-P" p. 237, "chlorpropham" p. 205, "thiocarbazil" p. 229, "ethoxyfen" p. 30, "haloxyfop-P-methyl" p. 38, "haloxyfop-ethoxyethyl" p. 38, "flumiclorac-pentyl" p. 35, "flupropacil" p. 143, "nipyraclofen" p. 145, "metosulam" p. 33, "ethametsulfuron-methyl" p. 36, "thifensulfuron-methyl" p. 35 or in "Agricultural Chemicals", Book II Herbicides, 1993 see "thiobencarb" p. 85, "benzofenap" p. 221, "napropanilid" p. 49, "piperophos" p. 102, "anilofos" p. 241, "TH-913" p. 150, "HW-52" p. 54, "ICIA-0051" p. 268, "poast" p. 253, "focus" p. 222, "dimethenamid" p. 48, "sulfosaten " p. 236, "2,4-DB" p. 10, "dichlorprop-P" p. 6, "flupoxam" p. 44, "prosulfocarb" p. 84, "quinmerac" p. 233, "metazachlor" p. 64, "flurtamone" p. 265, "bromofenoxim" p. 228, "fomesafen" p. 248, "imazethabenz-methyl" p. 153, "clodinafop" p. 214, "fenoxaprop-P-ethyl" p. 208, "fluazifop-P-butyl" p. 207, "quizalofop-P-ethyl" p. 210, "quizalofop-terfuryl" p. 211, "flumioxazin" p. 43, "flumipropyn" p. 267, "sulfentrazone" p. 261, "thiazopyr" p. 226, "pyrithiobac-sodium" p. 266, "flumetsulam" p. 227, "amidosulfuron" p. 151, "halosulfuron-methyl" p. 148, "rimsulfuron" p. 138, "tribenuron-methyl" p. 139, "triflusulfuron-methyl" p. 137, "primisulfuron" p. 147 or in "Short Review of Herbicides & PGRs 1991, Hodogaya Chemicals see "furyloxyfen" p. 142, "triazofenamid" p. 268, "KH-218" p. 52, "NSK-850" p. 52, "JC-940" p. 90, "AC-92553" p. 58, "buthidazole" p. 88, "cyprazole" p. 38, "allidochlor" p. 48, "benzoylprop-ethyl" p. 38, "chlorthiamid" p. 150 "diphenamid" p. 34, "flamprop-methyl" p. 40, "fosamin" p. 232, "isoxaben" p. 42, "monalide" p. 32, "naptalam" p. 36, "pronamid" p. 34, "bialaphos" p. 234, "glufosinate-ammonium" p. 234, "glyphosates" p. 232, "amitrol" p. 254, "clomeprop" p. 20, "dichlorprop" p. 6, "fenoprop" p. 8, "fluroxypyr" p. 156, "MCPA" p. 4, "MCPB" p. 8, "mecoprop" p. 6, "napropamide" p. 16, "triclopyr" p. 154, "chloramben" p. 28, "dicamba" p. 26, "clomazone" p. 268, "diflufenican" p. 42, "fluorochloridone" p. 266, "fluridone" p. 156, "asulam" p. 112, "barban" p. 100, "butylate" p. 106, "carbetamide" p. 36, "chlorobufam" p. 100, "cycloate" p. 108, "desmedipham" p. 104, "di-allate" p. 106, "EPTC" p. 108, "orbencarb" p. 112, "pebulate" p. 106, "phenisopham" p. 118, "pendimedipham" p. 104, "propham" p. 100, "sulf-allate" p. 110, "terbucarb" p. 102, "tri-allate" p. 108, "vernolate" p. 108, "acetochlor" p. 48, "alachlor" p. 46, "diethathyl-ethyl" p. 48, "dimethachlor" p. 50, "metolachlor" p. 46, "propachlor" p. 44, "pyrnachlor" p. 44, "terbuchlor" p. 48, "xylachlor" p. 52, "alloxydim" p. 260, "clethodim" p. 270, "cloproxydim" p. 268, "tralkoxydim" p. 270, "dalapon" p. 212, "ethofumesate" p. 124, "benefin" p. 54, "butralin" p. 58, "dinitramin" p. 56, "ethalfluralin" p. 60, "fluchloralin" p. 54, "isopropalin" p. 58, "nitralin" p. 58, "oryzalin" p. 60, "prodiamine" p. 62, "profluralin" p. 54, "trifluralin" p. 54, "dinoseb" p. 128, "dinoseb-acetate" p. 128, "dinoterb" p. 128, "DNOC" p. 126, "acilfluorfen-sodium" p. 142, "aclonifen" p. 146, "bifenox" p. 140, "chlornitrofen" p. 138, "difenoxuron" p. 76, "fluorodifen" p. 138, "fluoroglycofen-ethyl" p. 146, "lactofen" p. 144, "nitrofen" p. 136, "nitrofluorfen" p. 140, "oxyfluorfen" p. 140, "cyperquat" p. 158, "difenzoquat" p. 160, "diquat" p. 158, "paraquat" p. 158, "benzthiazuron" p. 82, "buturon" p. 66, "chlorbromuron" p. 72, "chloroxuron" p. 76, "chlortoluron" p. 74, "cycluron" p. 84, "dimeturon" p. 88, "diuron" p. 70, "ethidimuron" p. 86, "fenuron" p. 64, "fluometuron" p. 68, "isoproturon" p. 80, "isouron" p. 88, "karbutilate" p. 76, "linuron" p. 72, "methabenzthiazuron" p. 82, "metoxuron" p. 72, "monolinuron" p. 66, "monuron" p. 64, "neburon" p. 72, "siduron " p. 68, "tebuthiuron" p. 86, "trimeturon" p. 64, "isocarbamid" p. 168, "imazamethapyr" p. 172, "imazapyr" p. 170, "imazaquin" p. 170, "imazethapyr" p. 172, "methazole" p. 162, "oxadiazon" p. 162, "tridiphane" p. 266, "bromoxynil" p. 148, "ioxynil" p. 148, "diclofop-methyl" p. 16, "fenthiaprop-ethyl" p. 20, "fluazifop-butyl" p. 18, "haloxyfop-methyl" p. 18, "isoxapyrifop" p. 22, "propaquizafop" p. 24, "quizalofop-ethyl" p. 20, "chlorfenac" p. 258, "chlorophenprop-methyl" p. 258, "chloridazon" p. 174, "maleic hydrazide" p. 162, "norflurazon" p. 174, "pyridate" p. 176, "clopyralid" p. 154, "picloram," p. 154, "chlorimuron-ethyl" p. 92, "chlorsulfuron" p. 92, "flazasulfuron" p. 96, "metsulfuron-methyl" p.92, "nicosulfuron" p. 96, "sulfometuron-methyl" p. 92, "triasulfuron" p. 94, "ametryn" p. 198, "atrazine" p. 188, "aziprotryne" p. 206, "cyanazine" p. 192, "cyprazine" p. 192, "desmetryne" p. 200, "dipropetryn" p. 202, "eglinazine-ethyl" p. 208, "hexazinon" p. 208, "procyazine" p. 192, "prometone" p. 196, "prometryn" p. 196, "propazine" p. 188 "secbumeton" p. 196, "simazine" p. 188, "simetryn" p. 196, "terbumeton" p. 204, "terbutryn" p. 198, "terbuthylazine" p. 190, "trietazine" p. 188, "ethiozin" p. 210, "metamitron" p. 206, "metribuzin" p. 202, "bromacil" p. 180, "lenacil" p. 180, "terbacil" p. 180, "benazolin" p. 262, "bensulide" p. 228, "benzofluor" p. 266, "butamifos" p. 228, "DCPA" p. 28, "dichlobenil" p. 148, "endothal" p. 264, "mefluidide" p. 306, "perfluidone" p. 260, "terbuchlor" p. 48 or in "Global Herbicide Directory" First Edition, 1994 see "oxadiargyl" p. 96, or in "European Directory of Agrochemical Products Volume 2—Herbicides" Fourth Edition, see "buminafos" p. 255. The compound "DEH-112" is disclosed in European Patent Application EP 0 302 203. The compound "caloxydim" is described in DE 3 336 140, the compound "cinidon-ethyl" in DE 3 603 789 and the compound "fluorbentranil" in EP 84 893. "Other compounds are known from "Brighton Crop Protection Conference—Weeds —1993 (see "thidiazimin" p. 29, "AC-322140" p. 41, "KIH-6127" p. 47, "prosulfuron" p. 53, "KIH-2023" p. 61, "metobenzuron" p. 67). The compound "CH-900" is described in EP 0 332 133.

In principle, it is desirable in crop protection products to increase the specific activity of an active ingredient and the reliability of its action. It was therefore the object of the present invention to increase the activity of known, herbicidally active sulfonylureas of the formula I.

We have found that this object is achieved by a herbicidal mixture which comprises.

a) at least one derivative of the sulfonylurea of the formula I:

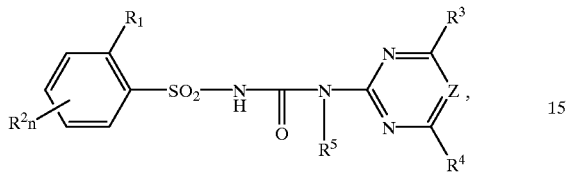

(I)

where the substituents have the following meanings:

$R^1$ is $C_1$–$C_6$-alkyl which has attached to it one to five of the following groups: methoxy, ethoxy, $SO_2CH_3$, cyano, chlorine, fluorine, $SCH_3$, $S(O)CH_3$; halogen; a group $ER^6$ where E is O, S or $NR^7$; $COOR^8$; $NO_2$; $S(O)_oR^9$, $SO_2NR^{10}R^{11}$, $CONR^{10}R^{11}$;

$R^2$ is hydrogen, $C_1$–$C_4$-alkyl, $C_2$–$C_4$-alkenyl, $C_2$–$C_4$-alkynyl, halogen, $C_1$–$C_4$-alkoxy, $C_1$–$C_4$-haloalkoxy; $C_1$–$C_4$-haloalkyl, a $C_1$–$C_2$-alkylsulfonyl group, nitro, cyano or $C_1$–$C_4$-alkylthio;

$R^3$ is F, $CF_3$, $CF_2Cl$, $CF_2H$, $OCF_3$, $OCF_2Cl$, or, if $R^1$ is $CO_2CH_3$ and $R^2$ is simultaneosly fluorine, $R^3$ is Cl, or, if $R^1$ is $CH_2CF_3$ or $CF_2CF_3$, $R^3$ is methyl, or, if $R^4$ is $OCF_3$ or $OCF_2Cl$, $R^3$ is $OCF_2H$ or OCF2Br;

$R^4$ is $C_1$–$C_2$-alkoxy, $C_1$–$C_2$-alkyl, $C_1$–$C_2$-alkylthio, $C_1$–$C2$-alkylamino, di-$C_1$–$C_2$-alkylamino, halogen, $C_1$–$C_2$-haloalkyl, $C_1$–$C_2$-haloalkoxy, $R^5$ is hydrogen, $C_1$–$C_2$-alkoxy, $C_1$–$C_4$-alkyl;

$R^6$ is $C_1$–$C_4$-alkyl, $C_2$–$C_4$-alkenyl, $C_2$–$C_4$-alkynyl or $C_3$–$C_6$-cycloalkyl, all of which can have attached to them. 1 to 5 halogen atoms, with the exception of allyl, difluoromethoxy, chlorodifluoromethoxy and 2-chloroethoxy, if E is O or S. In the event that E is O or $NR^7$, $R^6$ is furthermore also methylsulfonyl, ethylsulfonyl, trifluoromethylsulfonyl, allylsulfonyl, propargylsulfonyl or dimethylsulfamoyl;

$R^7$ is hydrogen, methyl or ethyl $R^8$ is a $C_1$–$C_6$-alkyl group which can have attached to it up to three of the following radicals: halogen, $C_1$–$C_4$-alkoxy, $C_1$–$C_4$-alkylthio, $C_1$–$C_4$-haloalkoxy, $C_1$–$C_4$-alkoxy-$C_1$–$C_2$-alkoxy, $C_3$–$C_7$-cycloalkyl and/or phenyl; a $C_5$–$C_7$-cycloalkyl group which can have attached to it up to three $C_1$–$C_4$-alkyl groups; $C_3$–$C_6$-alkenyl or $C_3$–$C_6$-alkynyl;

$R^9$ is a $C_1$–$C_6$-alkyl group which can have attached to it one to three of the following radicals: halogen, $C_1$–$C_4$-alkoxy, $C_1$–$C_4$-alkylthio, $C_1$–$C_4$-haloalkoxy, $C_1$–$C_4$-alkoxy-$C_1$–$C_2$-alkoxy, $C_3$–$C_7$-cycloalkyl and/or phenyl; a $C_5$–$C_7$-cycloalkyl group which can have attached to it one to three $C_1$–$C_4$-alkyl groups; a $C_3$–$C_6$-alkenyl group or a $C_3$–$C_6$-alkynyl group;

$R^{10}$ is hydrogen, a $C_1$–$C_2$-alkoxy group, a $C_1$–$C_6$-alkyl group, or together with $R^{11}$ is a $C_4$–$C_6$-alkylene chain in which one methylene group can be replaced by an oxygen atom or a $C_1$–$C_4$-alkylimino group;

$R^{11}$ is a $C_1$–$C_4$-alkyl group which can have attached to it one to four halogen or $C_1$–$C_4$-alkoxy radicals; $C_3$–$C_6$-cycloalkyl n is 0–3 o is 1–2

Z N or CH, and b) a synergistically active amount of at least one herbicidal compound selected from the groups b1 to b41 b1 1,3,4-thiadiazoles: buthidazole, cyprazole b2 amides: allidochlor (CDAA), benzoylprop-ethyl, bromobutide, chlorthiamid, dimepiperate, dimethenamid, diphenamid, etobenzanid (benzchlomet), flamprop-methyl, fosamin, isoxaben, monalide, naptalame, pronamid (propyzamid), propanil b3 aminophosphoric acids: bilanafos, (bialaphos), buminafos, glufosinate-ammonium, glyphosate, sulfosate b4 aminotriazoles: amitrol b5 anilides: anilofos, mefenacet b6 aryloxyalkanoic acids: 2,4-D, 2,4-DB, clomeprop, dichlorprop, dichlorprop-P, dichlorprop-P (2,4-DP-P), fenoprop (2,4,5-TP), fluoroxy-pyr, MCPA, MCPB, mecoprop, mecoprop-P, napropamide, napropanilide, triclopyr b7 benzoic acids: chloramben, dicamba b8 benzothiadiazinones: bentazone b9 bleaches: clomazone (dimethazone), diflufenican, fluorochloridone, flupoxam, fluridone, pyrazolate, sulcotrione (chlormesulone)

b10 carbamates: asulam, barban, butylate, carbetamid, chlorbufam, chlorpropham, cycloate, desmedipham, di-allate, EPTC, esprocarb, molinate, orbencarb, pebulate, phenisopham, phenmedipham, propham, prosulfocarb, pyributicarb, sulf-allate (CDEC), terbucarb, thiobencarb (benthiocarb), tiocarbazil, tri-allate, vernolate b11 quinolinecarboxylic acids: quinclorac, quinmerac b12 chloracetanilides: acetochlor, alachlor, butachlor, butenachlor, diethatylethyl, dimethachlor, metazachlor, metolachlor, pretilachlor, propachlor, prynachlor, terbuchlor, thenylchlor, xylachlor b13 cyclohexenones: alloxydim, caloxydim, clethodim, cloproxydim, cycloxydim, sethoxydim, tralkoxydim, 2-{1-[2-(4-chlorophenoxy)propyloxyimino]butyl}-3-hydroxy-5-(2H-tetrahydrothiopyran-3-yl)-2-cyclohexen-1-one b14 dichloropropionic acids: dalapon b15 dihydrobenzofurans: ethofumesate b16 dihydrofuran-3-ones: flurtamone b17 dinitroanilines: benefin, butralin, dinitramin, ethalfluralin, fluchloralin, isopropalin, nitralin, oryzalin, pendimethalin, prodiamine, profluralin, trifluralin b18 dinitrophenols: bromofenoxim, dinoseb, dinoseb-acetate, dinoterb, DNOC b19 diphenyl ethers: acifluorfen-sodium, aclonifen, bifenox, chlornitrofen (CNP), difenoxuron, ethoxyfen, fluorodifen, fluoroglycofen-ethyl, fomesafen, furyloxyfen, lactofen, nitrofen, nitrofluorfen, oxyfluorfen b20 dipyridylenes: cyperquat, difenzoquat methylsulfate, diquat, paraquat dichloride b21 ureas: benzthiazuron, buturon, chlorbromuron, chloroxuron, chlortoluron, cumyluron, dibenzyluron, cycluron, dimefuron, diuron, dymrone, ethidimuron, fenuron, fluometuron, isoproturon, isouron, karbutilate, linuron, methabenzthiazuron, metobenzuron, metoxuron, monolinuron, monuron, neburon, siduron, tebuthiuron, trimeturon b22 imidazoles: isocarbamid b23 imidazolinones: imazamethapyr, imazapyr, imazaquin, imazethabenz-methyl (imazame), imazethapyr b24 oxadiazoles: methazole, oxadiargyl, oxadiazon
b25 oxiranes: tridiphane
b26 phenols: bromoxynil, ioxynil
b27 phenoxyphenoxypropionic esters: clodinafop, cyhalofop-butyl, diclofop-methyl, fenoxapropethyl, fenoxaprop-P-ethyl, fenthiapropethyl, fluazifopbutyl, fluazifop-P-butyl, haloxyfop-ethoxyethyl, haloxy-fop-methyl, haloxyfop-P-methyl, isoxapyrifop, propaquizafop, quizalofop-ethyl, quizalofop-P-ethyl, quizalofop-tefuryl
b28 phenylacetic acids: chlorfenac (fenac)
b29 phenylpropionic acid: chlorophenprop-methyl
b30 protoporphyrinogen IX oxydase inhibitors: benzofenap, cinidon-ethyl, flumiclorac-pentyl, flumioxazin, flumipropyn, flupropacil, fluthiacet-methyl, pyrazoxyfen, sulfentrazone, thidiazimin
b31 pyrazoles: nipyraclofen
b32 pyridazines: chloridazon, maleic hydrazide, norflurazon, pyridate
b33 pyridinecarboxylic acids: clopyralid, dithiopyr, picloram, thiazopyr
b34 pyrimidyl ethers: pyrithiobac acid, pyrithiobac sodium, KIH-2023, KIH-6127
b35 sulfonamides: flumetsulam, metosulam
b36 sulfonylureas: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl
b37 triazines: ametryn, atrazine, aziprotryn, cyanazine, cyprazine, desmetryn, dimethamethryn, dipropetryn, eglinazine-ethyl, hexazinon, procyazine, prometon, prometryn, propazine, secbumeton, simazine, simetryn, terbumeton, terbutryn, terbuthylazine, trietazine
b38 triazinones: ethiozin, metamitron, metribuzin
b39 triazolecarboxamides: triazofenamid
b40 uracils: bromacil, lenacil, terbacil
b41 others: benazolin, benfuresate, bensulide, benzofluor, butamifos, cafenstrole, chlorthal-dimethyl (DCPA), cinmethylin, dichlobenil, endothall, fluorbentranil, mefluidide, perfluidone, piperophos
or their environmentally compatible salts.

The herbicidal mixture according to the invention has superadditive synergistic action and is selective for those crop plants which also tolerate the individual compounds themselves.

Especially preferred sulfonylureas of the formula I with a view to their synergistic herbicidal action are those where
$R^1$ is $CO_2CH_3$, $CO_2C_2H_5$, $CO_2iC_3H_7$, $CF_3$, $CF_2H$; $OSO_2CH_3$, $OSO_2N(CH_3)_2$, $Cl$, $NO_2$, $SO_2N(CH_3)_2$, $SO_2CH_3$ and $N(CH_3)SO_2CH_3$
$R^2$ is hydrogen, Cl, F or $C_1$–$C_2$-alkyl
$R^3$ is $CF_2H$, $OCF_3$, $OCF_2Cl$, $CF_2Cl$, $CF_3$ or F
$R^4$ is $OCH_3$, $OC_2H_5$, $OCF_3$, $OCF_2Cl$; $CF_3$, Cl, F, $NH(CH_3)$, $N(CH_3)_2$ or $C_1$–$C_2$-alkyl
$R^5$ hydrogen,
Z N or CH and
n 0 or 1.
preferred compounds of the formula I are compiled in the table which follows.

TABLE

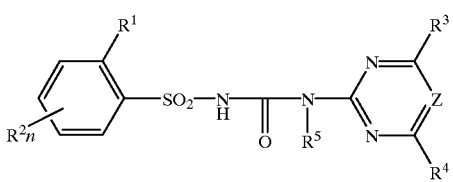

| No. | $R^1$ | $R^2$ | $R^5$ | $R^3$ | $R^4$ | Z |
|---|---|---|---|---|---|---|
| 1 | $CO_2CH_3$ | H | H | $OCF_2Cl$ | $OCH_3$ | CH |
| 2 | $CO_2C_2H_5$ | H | H | $OCF_2Cl$ | $OCH_3$ | CH |
| 3 | $CO_2iC_3H_7$ | H | H | $OCF_2Cl$ | $OCH_3$ | CH |
| 4 | $NO_2$ | H | H | $OCF_2Cl$ | $OCH_3$ | CH |
| 5 | $SO_2CH_3$ | H | H | $OCF_2Cl$ | $OCH_3$ | CH |
| 6 | $SO_2N(CH_3)_2$ | H | H | $OCF_2Cl$ | $OCH_3$ | CH |
| 7 | Cl | H | H | $OCF_2Cl$ | $OCH_3$ | CH |
| 8 | $N(CH_3)SO_2CH_3$ | H | H | $OCF_2Cl$ | $OCH_3$ | CH |
| 9 | $OSO_2CH_3$ | H | H | $OCF_2Cl$ | $OCH_3$ | CH |
| 10 | $OSO_2N(CH_3)_2$ | H | H | $OCF_2Cl$ | $OCH_3$ | CH |
| 11 | $CF_3$ | H | H | $OCF_2Cl$ | $OCH_3$ | CH |
| 12 | $CF_2H$ | H | H | $OCF_2Cl$ | $OCH_3$ | CH |
| 13 | $CO_2CH_3$ | H | H | $OCF_3$ | $OCH_3$ | CH |
| 14 | $CO_2C_2H_5$ | H | H | $OCF_3$ | $OCH_3$ | CH |
| 15 | $CO_2iC_3H_7$ | H | H | $OCF_3$ | $OCH_3$ | CH |
| 16 | $NO_2$ | H | H | $OCF_3$ | $OCH_3$ | CH |
| 17 | $SO_2CH_3$ | H | H | $OCF_3$ | $OCH_3$ | CH |
| 18 | $SO_2N(CH_3)_2$ | H | H | $OCF_3$ | $OCH_3$ | CH |
| 19 | Cl | H | H | $OCF_3$ | $OCH_3$ | CH |
| 20 | $N(CH_3)SO_2CH_3$ | H | H | $OCF_3$ | $OCH_3$ | CH |
| 21 | $OSO_2CH_3$ | H | H | $OCF_3$ | $OCH_3$ | CH |
| 22 | $OSO_2N(CH_3)_2$ | H | H | $OCF_3$ | $OCH_3$ | CH |
| 23 | $CF_3$ | H | H | $OCF_3$ | $OCH_3$ | CH |
| 24 | $CF_2H$ | H | H | $OCF_3$ | $OCH_3$ | CH |
| 25 | $CO_2CH_3$ | H | H | F | $OCH_3$ | CH |
| 26 | $CO_2C_2H_5$ | H | H | F | $OCH_3$ | CH |
| 27 | $CO_2iC_3H_7$ | H | H | F | $OCH_3$ | CH |
| 28 | $NO_2$ | H | H | F | $OCH_3$ | CH |
| 29 | $SO_2CH_3$ | H | H | F | $OCH_3$ | CH |
| 30 | $SO_2N(CH_3)_2$ | H | H | F | $OCH_3$ | CH |
| 31 | Cl | H | H | F | $OCH_3$ | CH |
| 32 | $N(CH_3)SO_2CH_3$ | H | H | F | $OCH_3$ | CH |
| 33 | $OSO_2CH_3$ | H | H | F | $OCH_3$ | CH |
| 34 | $OSO_2N(CH_3)_2$ | H | H | F | $OCH_3$ | CH |
| 35 | $CF_3$ | H | H | F | $OCH_3$ | CH |
| 36 | $CF_2H$ | H | H | F | $OCH_3$ | CH |
| 37 | $CO_2CH_3$ | H | H | $CF_3$ | $OCH_3$ | N |
| 38 | $CO_2C_2H_5$ | H | H | $CF_3$ | $OCH_3$ | N |
| 39 | $CO_2iC_3H_7$ | H | H | $CF_3$ | $OCH_3$ | N |
| 40 | $NO_2$ | H | H | $CF_3$ | $OCH_3$ | N |
| 41 | $SO_2CH_3$ | H | H | $CF_3$ | $OCH_3$ | N |
| 42 | $SO_2N(CH_3)_2$ | H | H | $CF_3$ | $OCH_3$ | N |
| 43 | Cl | H | H | $CF_3$ | $OCH_3$ | N |
| 44 | $N(CH_3)SO_2CH_3$ | H | H | $CF_3$ | $OCH_3$ | N |
| 45 | $OSO_2CH_3$ | H | H | $CF_3$ | $OCH_3$ | N |
| 46 | $OSO_2N(CH_3)_2$ | H | H | $CF_3$ | $OCH_3$ | N |
| 47 | $CF_3$ | H | H | $CF_3$ | $OCH_3$ | N |
| 48 | $CF_2H$ | H | H | $CF_3$ | $OCH_3$ | N |
| 49 | $CO_2CH_3$ | H | H | $CF_3$ | $OCH_3$ | CH |
| 50 | $CO_2C_2H_5$ | H | H | $CF_3$ | $OCH_3$ | CH |
| 51 | $CO_2iC_3H_7$ | H | H | $CF_3$ | $OCH_3$ | CH |
| 52 | $NO_2$ | H | H | $CF_3$ | $OCH_3$ | CH |
| 53 | $SO_2CH_3$ | H | H | $CF_3$ | $OCH_3$ | CH |
| 54 | $SO_2N(CH_3)_2$ | H | H | $CF_3$ | $OCH_3$ | CH |
| 55 | Cl | H | H | $CF_3$ | $OCH_3$ | CH |
| 56 | $N(CH_3)SO_2CH_3$ | H | H | $CF_3$ | $OCH_3$ | CH |
| 57 | $OSO_2CH_3$ | H | H | $CF_3$ | $OCH_3$ | CH |
| 58 | $OSO_2N(CH_3)_2$ | H | H | $CF_3$ | $OCH_3$ | CH |
| 59 | $CF_3$ | H | H | $CF_3$ | $OCH_3$ | CH |
| 60 | $CF_2H$ | H | H | $CF_3$ | $OCH_3$ | CH |
| 61 | $CO_2CH_3$ | H | H | $CF_2H$ | $OCH_3$ | N |
| 62 | $CO_2C_2H_5$ | H | H | $CF_2H$ | $CCH_3$ | N |
| 63 | $CO_2iC_3H_7$ | H | H | $CF_2H$ | $OCH_3$ | N |
| 64 | $NO_2$ | H | H | $CF_2H$ | $OCH_3$ | N |
| 65 | $SO_2CH_3$ | H | H | $CF_2H$ | $OCH_3$ | N |
| 66 | $SO_2N(CH_3)_2$ | H | H | $CF_2H$ | $OCH_3$ | N |
| 67 | Cl | H | H | $CF_2H$ | $OCH_3$ | N |

TABLE-continued

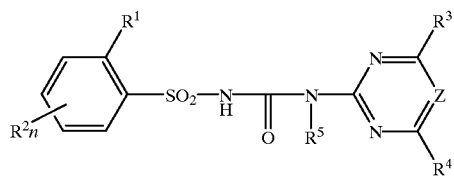

| No. | R¹ | R² | R⁵ | R³ | R⁴ | Z |
|---|---|---|---|---|---|---|
| 68 | $N(CH_3)SO_2CH_3$ | H | H | $CF_2H$ | $OCH_3$ | N |
| 69 | $OSO_2CH_3$ | H | H | $CF_2H$ | $OCH_3$ | N |
| 70 | $OSO_2N(CH_3)_2$ | H | H | $CF_2H$ | $OCH_3$ | N |
| 71 | $CF_3$ | H | H | $CF_2H$ | $OCH_3$ | N |
| 72 | $CF_2H$ | H | H | $CF_2H$ | $OCH_3$ | N |
| 73 | $CO_2CH_3$ | H | H | $CF_2H$ | $OCH_3$ | CH |
| 74 | $CO_2C_2H_5$ | H | H | $CF_2H$ | $OCH_3$ | CH |
| 75 | $CO_2iC_3H_7$ | H | H | $CF_2H$ | $OCH_3$ | CH |
| 76 | $NO_2$ | H | H | $CF_2H$ | $OCH_3$ | CH |
| 77 | $SO_2CH_3$ | H | H | $CF_2H$ | $OCH_3$ | CH |
| 78 | $SO_2N(CH_3)_2$ | H | H | $CF_2H$ | $OCH_3$ | CH |
| 79 | Cl | H | H | $CF_2H$ | $OCH_3$ | CH |
| 80 | $N(CH_3)SO_2CH_3$ | H | H | $CF_2H$ | $OCH_3$ | CH |
| 81 | $OSO_2CH_3$ | H | H | $CF_2H$ | $OCH_3$ | CH |
| 82 | $OSO_2N(CH_3)_2$ | H | H | $CF_2H$ | $OCH_3$ | CH |
| 83 | $CF_3$ | H | H | $CF_2H$ | $OCH_3$ | CH |
| 84 | $CF_2H$ | H | H | $CF_2H$ | $OCH_3$ | CH |
| 85 | $CO_2CH_3$ | H | H | $CF_2Cl$ | $OCH_3$ | N |
| 86 | $CO_2C_2H_5$ | H | H | $CF_2Cl$ | $OCH_3$ | N |
| 87 | $CO_2iC_3H_7$ | H | H | $CF_2Cl$ | $OCH_3$ | N |
| 88 | $NO_2$ | H | H | $CF_2Cl$ | $OCH_3$ | N |
| 89 | $SO_2CH_3$ | H | H | $CF_2Cl$ | $OCH_3$ | N |
| 90 | $SO_2N(CH_3)_2$ | H | H | $CF_2Cl$ | $OCH_3$ | N |
| 91 | Cl | H | H | $CF_2Cl$ | $OCH_3$ | N |
| 92 | $N(CH_3)SO_2CH_3$ | H | H | $CF_2Cl$ | $OCH_3$ | N |
| 93 | $OSO_2CH_3$ | H | H | $CF_2Cl$ | $OCH_3$ | N |
| 94 | $OSO_2N(CH_3)_2$ | H | H | $CF_2Cl$ | $OCH_3$ | N |
| 95 | $CF_3$ | H | H | $CF_2Cl$ | $OCH_3$ | N |
| 96 | $CF_2H$ | H | H | $CF_2Cl$ | $OCH_3$ | N |
| 97 | $CO_2CH_3$ | 3-F | H | Cl | $OCH_3$ | CH |
| 98 | $CF_2CF_3$ | H | H | $CH_3$ | $OCH_3$ | N |
| 99 | $CF_2CF_3$ | H | H | $CH_3$ | $OCH_3$ | N |
| 100 | $SO_2C_2H_5$ | H | H | F | $OCH_3$ | CH |

Examples of preferred compounds (b) are:
bromobutide
dimethenamid
isoxaben
propanil
glufosinate-ammonium
glyphosate
sulfosate
mefenacet
2,4-D
2,4-DB
2,4-DBEE
dichlorprop
dichlorprop-P
dichlorprop-P (2,4-DP-P)
fluroxypyr
MCPA
mecoprop
mecoprop-P
dicama
bentazone
clomazone
diflufenican
sulcotrione
phenmedipham
thiobencarb
quinclorac
quinmerac
acetochlor
alachlor
butachlor
metazachlor
metolachlor
pretilachlor
butroxydim
caloxydim
clethodim
cycloxydim
sethoxydim
tralkoxydim
2-{1[-2-(4-chlorophenoxy)propyloxyimino]butyl}-3-hydroxy-5-(2H-tetrahydrothiopyran-3-yl)-2-cyclohexen-1-one
pendimethalin
acifluorfen-sodium
bifenox
fluoroglycofen-ethyl
fomesafen
lactofen
chlortoluron
cycluron
dymrone
isoproturon
methabenzthiazuron
imazaquin
imazethabenz-methyl
imazethapyr
bromoxynil
ioxynil
clodinafop
cyhalofop-butyl
fenoxyprop-ethyl
fenoxaprop-P-ethyl
haloxyfop-P-methyl
cinidon-ethyl
flumiclorac-pentyl
flumipropyn
fluthiacet-methyl
pyridate
clopyralid
bispyribac-sodium
KIH-8555
KUH-920
flumetsulam
metosulam
amidosulfuron
azimsulfuron
bensulfuron-methyl
chlorimuron-ethyl
chlorsulfuron
cinosulfuron
cyclosulfamuron
ethoxysulfuron
flazasulfuron
halosulfuron-methyl
HOE-107925
imazosulfuron
metsulfuron-methyl
nicosulfuron
primisulfuron
prosulfuron
pyrazosulfuron-ethyl
rimsulfuron
thifensulfuron-methyl
triasulfuron tribenuron-methyl
atrazine
cyanazine
terbuthylazine
benazolin
benfuresate
cafenstrole
cinemthylin
ammonium-bentazone
cloquintocet
ET-751
F-8426
KPP-314

The following compounds are particularly preferred:
2,4-D
dichlorprop-P
MCPA
mecoprop-P
dicamba
bentazone
diflufenican
sulcotrione
quinclorac
caloxydim
cycloxydim
sethoxydim
2-{1-[2-(4-chlorophenoxy)propyloxyimino]butyl}-3-hydroxy-5-(2H-tetrahydrothiopyran-3-yl)-2-cyclohexen-1-one
acifluorfen-sodium
fluoroglycofen-ethyl
bromoxynil
fenoxyprop-ethyl
cinidon-ethyl
amidosulfuron
bensulfuron-methyl
metsulfuron-methyl
nicosulfuron
pyrazosulfuron-ethyl
rimsulfuron
triasulfuron
tribenuron-methyl
atrazine
terbuthylazine
ammonium-bentazone
cloquintocet The following compounds are very especially preferred:
dichlorprop-P
mecoprop-P
ammonium-bentazone
bentazone
diflufenican
quinclorac
2-(1-[2-(4-chlorophenoxy)propyloxyimino]butyl)-3-hydroxy-5-(2H-tetrahydrothiopyran-3-yl)-2-cyclohexen-1-one
caloxydim
cycloxydim
sethoxydim
fluoroglycofen-ethyl
cinidon-ethyl
nicosulfuron
pyrazosulfuron-ethyl
rimsulfuron
atrazine
terbuthylazine.

The present invention also relates to herbicidal compositions which comprise at least one herbicidally active amount of a sulfonylurea (a) of the above-described formula I or their environmentally compatible salts, a synergistically active amount of at least one above-described herbicidal compound (b) or its environmentally compatible salts, at least one liquid and/or solid carrier and, if desired, at least one adjuvant.

In the herbicidal mixtures and herbicidal compositions according to the invention, the sulfonylureas of the formula I or their environmentally compatible salts and the herbicidal compounds (b) or their environmentally compatible salts are used in such weight ratios that the desired synergistic effect is observed. The mixing ratios of sulfonylurea of the formula I and a herbicidal compound (b) are preferably 1: to 1:0.1 to 1:40, in particular 1:0.2 to 1:20, especially preferably 1:0.5 to 1:15.

The herbicidal mixtures and herbicidal compositions according to the invention which comprise the sulfonylureas of the formula I or their environmentally compatible salts of, for example, alkali metals, alkaline earth metals or ammonia and amines and the herbicidal compounds (b) or their environmentally compatible salts of, for example, alkali metals, alkaline earth metals or ammonia and amines are capable of effecting very good control of broad-leaved weeds and grass weeds in the crop rice without damaging the crop plants, an effect which is observed even when low rates of application are used.

Taking into consideration the versatility of the application methods, the herbicidal mixtures and herbicidal compositions according to the invention can also be employed in a further number of crop plants for eliminating undesirable plants. Suitable crops are, for example, the following:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum (N.rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera, Zea mays,*

In addition, the herbicidal mixtures and herbicidal compositions according to the invention can also be used in crops which tolerate the action of herbicides due to breeding, including genetic engineering methods.

The herbicidal mixtures and herbicidal compositions according to the invention may be applied pre- or post-emergence. If the active ingredients are less well tolerated by certain crop plants, application techniques may be used in which the herbicidal compositions are sprayed, with the aid of the spraying equipment, in such a way that the active ingredients reach the leaves of the sensitive crop plants as little as possible while reaching the leaves of undesirable plants which grow underneath, or the bare soil surface (post-directed, lay-by).

The compositions according to the invention can be applied, for example in the form of ready-to-spray aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

Suitable inert additives are mineral oil fractions of medium to high boiling point, such as kerosene or diesel oil, furthermore coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, adhesive, dispersant or emulsifier. Alternatively, it is possible to prepare concentrates composed of active ingredient, wetting agent, adhesive, dispersant or emulsifier and, if desired, solvent or oil, which are suitable for dilution with water.

Suitable surfactants are the alkali, alkaline earth and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctylphenol, octylphenol or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for spreading, and dusts, can be prepared by mixing or concomitantly grinding the herbicidal mixture with a solid carrier.

Granules, eg. coated granules, impregnated granules and homogeneous granules, can be prepared by binding the active ingredient onto solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

In general, the formulations comprise 0.01 to 95% by weight, preferably 0.5 to 90% by weight, of the herbicidal mixture.

It may furthermore be advantageous to apply the herbicidal mixtures and herbicidal compositions according to the invention together in the form of a mixture with other crop protection agents, for example with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The rates of application of pure herbicidal mixture, ie. without formulation auxiliaries, are from 0.01 to 5 kg/ha, preferably 0.03 to 4 kg/ha, especially preferably 0.1 to 3.0 kg/ha, of active ingredient (a.i.), depending on the intended purpose, the season, the target plants and the growth stage.

The herbicidal compositions according to the invention are applied to the plants mainly by means of foliar sprays. They may be applied by customary spraying techniques using amounts of approximately 100 to 1000 l of spray mixture per ha, for example using water as the carrier. An application of the compositions in the so-called "low-volume" and "ultra-low-volume" method is also possible, as is their application in the form of so-called granules.

USE EXAMPLE

The herbicide mixtures were applied post-emergence (foliar treatment), the sulfonylurea derivatives being applied in the form of 10 to 75 percent granules and the herbicidal compounds (b) in the formulation in which they exist as the commercial product.

The tests involved field trials with small plots at a sandy loam site (pH 6.2 to 7.0) or sandy clay (pH 5.0 to 6.7) site.

The weeds were present in different sizes and development stages, their height being, on average, 5 to 20 cm, depending on the plant habit.

The herbicidal compositions were applied alone and also jointly, in the latter case sometimes as a tank mix, sometimes as a ready-mix. This was done using water (350 l/ha) as the distribution vehicle, depending on the formulation of the active ingredients in the form of emulsions, aqueous solutions or suspensions. Application was effected with the aid of a mobile plot sprayer.

The test period extended over 3 to 8 weeks, and the stands were also observed at later dates.

The damage caused by the herbicidal compositions was assessed using a scale from 0% to 100% in comparison with untreated control plots. Thus, 0 means no damage, and 100 means complete destruction of the plants.

The examples which follow show the activity of the herbicidal compositions which can be used according to the invention without excluding the possibility of other uses.

In these examples, the method of S. R. Colby (1967): Calculating synergistic and antagonistic responses of herbicide combinations, Weeds 15, 20 et seq. was used to determine the value E which can be expected when an action of the individual active ingredients is merely additive.

The calculation was carried out using the formula:

$$E = X + Y - \frac{XY}{100}$$

where
X=percentage activity using preparation A at a rate of application a
Y=percentage activity using preparation B at a rate of application b
E=expected activity (in %) caused by A+B at rate of application of a+b.
If the observed value exceeds the value E calculated using Colby's formula, a synergistic effect is present.

The herbicidal compositions according to the invention have a herbicidal activity which is higher than what can be expected when applying Colby's formula compared with the observed activities of the individual components . . . used alone.

We claim:

1. A herbicidal composition comprising:

a) at least one sulfonylurea of the formula I:

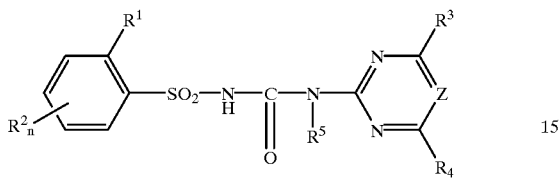

(I)

wherein:

$R^1$ is $C_1$–$C_6$-alkyl which carries one to five of the following groups: methoxy, ethoxy, $SO_2CH_3$, cyano, chlorine, fluorine $SCH_3$, $S(O)CH_3$; halogen; a group $ER^6$ where E is O, S or $NR^7$; $COOR^8$; $N_2$; $S(O)_oR^9$; $SO_2NR^{10}R^{11}$; $CONR^{10}R^{11}$;

$R^2$ is hydrogen, $C_1$–$C_4$-alkyl, $C_2$–$C_4$-alkenyl, $C_2$–$C_4$-alkynyl, halogen, $C_1$–$C_4$-alkoxy, $C_1$–$C_4$-haloalkoxy, $C_1$–$C_4$-haloalkyl, $C_1$–$C_2$-alkylsulfonyl, nitro, cyano or $C_1$–$C_4$-alkylthio;

$R^3$ is F, $CF_3$, $CF_2Cl$, $CF_2H$, $OCF_3$, $OCF_2Cl$ or, if $R^1$ is $CO_2CH_3$ and $R^2$ is simultaneously fluorine, $R^3$ is Cl, or, if $R^1$ is $CH_2CF_3$ or $CF_2CF_3$, $R^3$ is methyl, or, if $R^4$ is $OCF_3$ or $OCF_2Cl$, $R^3$ is $OCF_2H$ or $OCF_2Br$;

$R^4$ is $C_1$–$C_2$-alkoxy, $C_1$–$C_2$-alkyl, $C_1$–$C_2$-alkylthio, $C_1$–$C_2$-alkylamino, di-$C_1$–$C_2$-alkylamino, halogen, $C_1$–$C_2$-haloalkyl, $C_1$–$C_2$-haloalkoxy;

$R^5$ is hydrogen, $C_1$–$C_2$-alkoxy, $C_1$–$C_4$-alkyl;

$R^6$ is $C_1$–$C_4$-alkyl, $C_2$–$C_4$-alkenyl, $C_2$–$C_4$-alkynyl or $C_3$–$C_6$-cycloalkyl, where these groups may carry 1 to 5 halogen atoms, with the exception of allyl, difluoromethoxy, chlorodifluoromethoxy and 2-cloroethoxy when E is O or S; or in the event that E is O or $NR^7$, $R^6$ is furthermore methylsulfonyl, ethylsulfonyl, trifluoromethylsulfonyl, allylsulfonyl, propargylsulfonyl or dimethylsulfamoyl;

$R^7$ is hydrogen, methyl or ethyl;

$R^8$ is $C_1$–$C_6$-alkyl, which may carry up to three of the following radicals: halogen, $C_1$–$C_4$-alkoxy, $C_1$–$C_4$-alkylthio, $C_1$–$C_4$-haloalkoxy, $C_1$–$C_4$-alkoxy-$C_1$–$C_4$-alkoxy, $C_3$–$C_7$-cycloalkyl and/or phenyl; $C_5$–$C_7$-cycloalkyl which may carry up to three $C_1$–$C_4$-alkyl groups; $C_3$–$C_6$-alkenyl or $C_3$–$C_6$-alkynyl;

$R^9$ is $C_1$–$C_6$-alkyl, which may carry up to three of the following radicals: halogen, $C_1$–$C_4$-alkoxy, $C_1$–$C_4$-alkylthio, $C_1$–$C_4$-haloalkoxy, $C_1$–$C_4$-alkoxy-$C_1$–$C_4$-alkoxy, $C_3$–$C_7$-cycloalkyl and/or phenyl $C_5$–$C_7$-cycloalkyl which may carry up to three $C_1$–$C_4$-alkyl groups; $C_3$–$C_6$-alkenyl or $C_3$–$C_6$-alkynyl;

$R^{10}$ is hydrogen, $C_1$–$C_2$-alkoxy, $C_1$–$C_6$-alkyl, or together with $R^{11}$ is a $C_4$–$C_6$-alkylene, chain in which one methylene group may be replaced by an oxygen atom or a $C_1$–$C_4$-alkylimino group;

$R^{11}$ is $C_1$–$C_4$-alkyl which may carry one to four halogen or $C_1$–$C_4$-alkoxy radicals; $C_3$–$C_6$-cycloalkyl;

n 0–3;

o is 1 or 2;

Z is N or CH, or an enviromentally compatible salt of I, and b) at least one herbicidal compound selected from groups $b_2$, $b_7$ to $b_9$, $b_{21}$, $b_{26}$, $b_{27}$, $b_{30}$, $b_{36}$ and $b_{37}$:

$b_2$) amides: allidochlor (CDAA), benzoylprop-ethyl, bromobutide, clorthiamid, dimepiperate, dimethenamid, diphenamid, etobenzanid (benzchlomet), flamprop-methyl, fosamin, isoxaben, monalide, naptalame, propamid (propyzamid and propanil;

$b_7$) benozoic acids: cloramben and dicamba;

$b_8$) benzothiadiazinones: bentazone;

$b_9$) bleachers: clomazone (dimethazone), diflufenican, flurocloridone, flupoxam, fluridone, pyrazolate and sulcotrione (clormesulone);

$b_{21}$) ureas: benzthiazuron, buturon, chlorbromuron, chloroxuron, chlortoluron, cumyluron, bibenzyluron, cycluron, dimefuron, diuron, dymrone, ethidimuron, fenuron, fluormeturon, isoproturon, isouron, karbutilate, linuron, methabenzthiazuron, metobenzuron, metoxuron, monolinuron, monuron, siduron, tebuthiuron and trimeturon;

$b_{26}$) phenols: bromoxynil and ioxynil;

$b_{27}$) phenoxyphenoxypropionic esters: clodinafop, cyhalofop-butyl, diclofop-methyl, fenoxaprop-ethyl, fenoxapro-P-ethyl, fenthiaprop-ethyl, fluazifop-butyl, fluazifop-P-butuyl, haloxyfop-ethoxyethyl, haloxyfop-methyl, haloxyfop-P-methyl, isoxapyrifop, propaquizafop, quizalofop-ethyl, quizalofop-P-ethyl and quizalofop-tefuryl;

$b_{30}$) protoporphyrinogen IX oxidase inhibitors: benzofenap, cirnidon-ethyl, flumiclorac-pentyl, flumioxazin, flumipropyn, flupropacil, fluthiacet-methyl, pyrazoxyfen, sulfentrazone and tridiazimin;

$b_{36}$) sulfonylureas: amidosulfuron, azimsulfuron, bensulfuron-methyl, clorimuron-ethyl, clorsulfuron, cinosulfuron, cyclosulfuron, ethametsulfuron-methyl, ethoxysulfuron, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl thifensulfuron-methyl, triasulfuron, tribenuron-methyl and trifusulfuron-methyl;

$b_{37}$) triazines: ametryn, atrazine, aziprotryn, cyanazine cyprazine, desmetryn, dimethamethryn, dipropetryn, eglinazine-ethyl, hexazinon, procyazine, prometon, prometryn, propazine, secbumeton, simazine, simetryn, terbumeton, terbutryn, terbuthylazine and trietazine;

or an enviromentally compatible salt of the herbicidal compound, in a synergistically active amount.

2. The herbicidal composition defined in claim 1, comprising a sulfonylurea of the formula I wherein:

$R^1$ is $CO_2CH_3$, $CO_2C_2H_5$, $CO_2iC_3H_7$, $CF_3$, $CF_2H$, $CH_2CF_3$, $CF_2CF_3$, $OSO_2CH_3$, $OSO_2N(CH_3)_2$, Cl, $NO_2$, $SO_2N(CH_3)_2$, $SO_2CH_3$, $SO_2C_2H_5$ and $N(CH_3)SO_2CH_3$, $R^2$ is hydrogen, halogen or methyl, $R^3$ is $CF_2H$, $OCF_3$, $OCF_2Cl$, $CF_3$, or, if $R^1$ is $CO_2CH_3$ and $R^2$ is simultaneously fluorine, $R^3$ is Cl, or, if $R^1$ is $CH_2CF_3$ or $CF_2CF_3$, $R^3$ is methyl, $R^4$ is $OCH_3$, and $R^5$ is hydrogen.

3. The herbicidal composition defined in claim 1, comprising a sulfonylurea of the formula I wherein:

$R^1$ is halogen, a group $ER^6$, $CO_2R^8$, $SO_2CH_3$ or $SO_2C_2H_5$, $R^2$ is hydrogen,
$R^3$ is F,
$R^4$ is $OCF_3$, $OCF_2Cl$ or $OCH_3$, and
$R^5$ is hydrogen.

4. The herbicidal composition defined in claim 1, comprising a sulfonylurea of the formula I wherein:
$R^1$ is $CF_3$,
$R^2$ is hydrogen,
$R^3$ is $CF_3$,
$R^4$ is $OCH_3$,
$R^5$ is hydrogen, and
Z is N.

5. The herbicidal composition defined in claim 1, wherein the herbicidal compound (b) is selected from the group consisting of:
bromobutide, dimethenamid, isoxaben, propanil, dicamba, bentazone, clomazone, diflufenican, flurochloridone, sulcotrione, chlortoluron, cycluron, dymrone, isoproturon, methabenzthiazuron, bromoxynil, ioxynil, clodinafop, cyhalofop-butyl, fenoxaprop-ethyl, fenoxaprop-p-ethyl, haloxyfop-p-methyl, cinidon-ethyl, flumiclorac-pentyl, flumipropyn, fluthiacet-methyl, amidosulfuron, azimsulfuron, bensulfuron-methyl, chlorimuron-ethyl, chlorsulfuron, cinosulfuron, cyclosulfuron, ethoxysulfuron, flazasulfuron, halosulfuron-methyl, imazosulfuron, metsulfuron-methyl, nicosulfuron, primisulfuron, prosulfuron, pyrazosulfuron-ethyl, rimsulfuron, thifensulfuron-methyl, triasulfuron, tribenuron-methyl, atrazine, cyanazine, terbutylazine, ammonium-bentazone, cloquintocet, ET-751, F-8426 and KPP-314.

6. The herbicidal composition defined in claim 1, wherein the herbicidal compound (b) is selected from the group consisting of:
dicamba, bentazone, diflufenican, sulcotrione, bromoxynil, fenoxaprop-ethyl, cinidon-ethyl, amidosulfuron, bensulfuron-methyl, metsulfuron-methyl, nicosulfuron, pyrazosulfuron-ethyl, rimsulfuron, triasulfuron, tribenuron-methyl, atrazine, ammonium-bentazone and cloquintocet.

7. The herbicidal composition defined in claim 1, comprising the sulfonylurea (a) and the one or more herbicidal compounds (b) in a weight ratio of 1:0.1 to 1:40.

8. The herbicidal composition defined in claim 1, comprising the sulfonylurea (a) and the one or more herbicidal compounds (b) in a weight ratio of 1:0.1 to 1:20.

9. A herbicidal composition comprising
a) a herbicidally active amount on a sulfonylurea of the formula I as defined in claim 1,
b) a synergistically active amount of at least one of the herbicidal compounds (b) defined in claim 1,
at least one liquid or solid carrier and optionally at least one adjuvant.

10. The herbicidal composition defined in claim 9, wherein the sulfonylurea (a) and one or more of the herbicidal compounds (b) are present in a weight ratio of 1:0.1 to 1:40.

11. The herbicidal composition defined in claim 9, wherein the sulfonylurea (a) and one or more of the herbicidal compounds (b) are present in a weight ratio of 1:0.1 to 1:40.

12. The herbicidal composition defined in claim 1, wherein at least one of the herbicidal compounds (b) is a benzoic acid selected from the group consisting of cloramben and dicamba.

13. The herbicidal composition defined in claim 12, wherein the weight ratio of the sulfonylurea to the benzoic acid is from 1:0.1 to 1:40.

14. The herbicidal composition defined in claim 12, wherein the weight ratio of the sulfonylurea to benzoic acid is from 1:0.2 to 1:20.

15. The herbicidal composition defined in claim 1, wherein component b) is at least one compound selected from the groups:
$b_2$) amides: dimethenamid;
$b_7$) benzoic acids: cloramben and dicamba;
$b_8$) benzothiadiazinones: bentazone;
$b_9$) bleachers: clomazone (dimethazone), diflufenican and sulcotrione (chlormesulone);
$b_{21}$) ureas: benzthiazuron, buturon, chlorbromuron, chloroxuron, chlortoluron, cumyluron, bibenzyluron, cycluron, dimefuron, diuron, dymrone, ethidimuron, fenuron, fluormeturon, isoproturon, isouron, linuron, methabenzthiazuron, metobenzuron, metoxuron, monolinuron, monuron, siduron, tebuthiuron and trimeturon;
$b_{26}$) phenols: bromoxynil and ioxynil;
$b_{27}$) phenoxyphenoxypropionic esters: clodinafop, cyhalofop-butyl, diclofop-methyl, fenoxaprop-ethyl, fenoxaprop-P-ethyl, fenthiaprop-ethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl and quizalofop-tefuryl;
$b_{30}$) protoporphyrinogen IX oxidase inhibitors: cinidon-ethyl, flumiclorac-pentyl, flumioxazin, flumipropyn, fluthiacet-methyl, sulfentrazone and thidiazimin;
$b_{36}$) sulfonylureas: amidosulfuron, azimsulfuron, bensulfuron-methyl, chlorimuron-ethyl, chlorsulfuron, cinosulfuron, cyclosulfuron, ethametsulfuron-methyl, ethoxysulfuron, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl and triflusulfuron-methyl;
$b_{37}$) triazines: atrazine, aziprotryn, cyanazine, cyprazine, desmetryn, dimethamethryn, dipropetryn, eglinazine-ethyl, procyazine, prometon, prometryn, propazine, secbumeton, simazine, simetryn, terbumeton, terbutryn, terbuthylazine and trietazine.

16. The herbicidal composition defined in claim 1, wherein component b) is at least one compound selected from the groups:
$b_2$) amides: dimethenamid;
$b_7$) benzoic acids: dicamba;
$b_8$) benzothiadiazinones: bentazone;
$b_9$) bleachers: clomazone (dimethazone), diflufenican and sulcotrione (chlormesulone);
$b_{21}$) ureas: diuron, dymrone, isoproturon, methabenzthiazuron and metoxuron;
$b_{26}$) phenols: bromoxynil and ioxynil;
$b_{27}$) phenoxyphenoxypropionic esters: clodinafop, diclofop-methyl, fenoxaprop-ethyl, fenoxaprop-P-ethyl, fluazifop-butyl, fluazifop-P-butyl, haloxyfop-methyl and haloxyfop-P-methyl;
$b_{30}$) protoporphyrinogen IX oxidase inhibitors: cinidon-ethyl, flumioxazin, fluthiacet-methyl and sulfentrazone;

b$_{36}$) sulfonylureas: amidosulfuron, chlorsulfuron, flazasulfuron, halosulfuron-methyl, metsulfuron-methyl, nicosulfuron, primisulfuron, prosulfuron, rimsulfuron, sulfometuron-methyl, thifensulfuron-methyl, triasulfuron and tribenuron-methyl;

b$_{37}$) triazines: atrazine, cyanazine, simazine and terbuthylazine.

17. The herbicidal composition defined in claim 1, wherein component b) is at least one compound selected from the group of: dicamba, bentazone, sulcotrione (chlormesulone), dimethenamid, isoproturon, bromoxynil, fenoxaprop-P-ethyl, clodinafop, cinidon-ethyl, halosulfuron-methyl and atrazine.

18. The herbicidal composition defined in claim 1, comprising a) a sulfonylurea of formula (I) wherein R$^1$ is trifluoromethyl, R$^2$ is hydrogen, R$^3$ is trifluoromethyl, R$^4$ is methoxy, R$^5$ is hydrogen and Z is nitrogen, and b) at least one compound selected from the group of: dicamba, bentazone, sulcotrione (chlormesulone), dimethenamid, isoproturon, bromoxynil, fenoxaprop-P-ethyl, clodinafop, cinidon-ethyl, halosulfuron-methyl and atrazine.

19. A method of controlling undesirable vegetation, which comprises applying the sulfonylurea (a) defined in claim 1 and one or more of the herbicidal compounds (b) defined in claim 1 before, during or after the emergence of undesirable plants, either simultaneously or in succession.

20. A method of controlling undesirable vegetation, which comprises treating the leaves of crop plants and of undesired plants with the sulfonylurea (a) defined in claim 1 and one or more of the herbicidal compounds (b) defined in claim 1, either simultaneously or in succession.

* * * * *

UNITED STATES PATENT AND TRADEMARK OFFICE
CERTIFICATE OF CORRECTION

PATENT NO.    : 6,362,133 B1
DATED         : March 7, 2000
INVENTOR(S)   : Landes et al.

It is certified that error appears in the above-identified patent and that said Letters Patent is hereby corrected as shown below:

Column 13,
Line 23, "$N_2$;" should be -- $NO_2$ --;
Line 55, "$C_2C_7$" should be -- $C_3$-$C_7$- --;
Line 64, "n 0-3;" should be -- n is 0-3; --.

Column 14,
Line 12, "flurocloridone" should be -- fluorochloridone --;
Line 13, "clormesulone" should be -- chlormesulone --;
Line 34, "clorimuron-ethyl, clorsulfuron" should be -- chlorimuron-ethyl, chlorsulfuron --;
Line 40, "methyl thifensulfuron" should be -- methyl, thifensulfuron --.

Signed and Sealed this

Twenty-fourth Day of September, 2002

Attest:

Attesting Officer

JAMES E. ROGAN
*Director of the United States Patent and Trademark Office*